(12) United States Patent
Emstad (10) Patent No.: US 9,314,348 B2
(45) Date of Patent: Apr. 19, 2016

(54) BILATERALLY EXPANDING INTERVERTEBRAL BODY FUSION DEVICE

(71) Applicant: Wenzel Spine, Inc., Austin, TX (US)

(72) Inventor: Erik Emstad, Austin, TX (US)

(73) Assignee: Wenzel Spine, Inc., Austin, TX (US)

( * ) Notice: Subject to any disclaimer, the term of this patent is extended or adjusted under 35 U.S.C. 154(b) by 0 days.

(21) Appl. No.: 14/730,876

(22) Filed: Jun. 4, 2015

(65) Prior Publication Data

US 2015/0351923 A1    Dec. 10, 2015

Related U.S. Application Data

(60) Provisional application No. 62/007,500, filed on Jun. 4, 2014.

(51) Int. Cl.
| | | |
|---|---|---|
| A61F 2/44 | (2006.01) | |
| A61F 2/46 | (2006.01) | |
| A61F 2/30 | (2006.01) | |

(52) U.S. Cl.
CPC ............. *A61F 2/446* (2013.01); *A61F 2/30771* (2013.01); *A61F 2/4611* (2013.01); *A61F 2002/3093* (2013.01); *A61F 2002/30904* (2013.01); *A61F 2002/4475* (2013.01); *A61F 2002/4623* (2013.01); *A61F 2002/4629* (2013.01); *A61F 2230/0067* (2013.01); *A61F 2230/0069* (2013.01)

(58) Field of Classification Search
CPC ................ A61F 2/44; A61F 2/46; A61F 2/30
USPC ........... 606/300–331, 86 A; 623/17.11–17.16
See application file for complete search history.

(56) References Cited

U.S. PATENT DOCUMENTS

| | | | |
|---|---|---|---|
| 1,000,715 | A | 8/1911 | Caywood |
| 1,286,285 | A | 12/1918 | Girvan |
| 2,159,580 | A | 5/1939 | Ziffer |
| 2,490,364 | A | 12/1949 | Livingston |
| 2,587,907 | A | 3/1952 | Schroeder |

(Continued)

FOREIGN PATENT DOCUMENTS

| | | |
|---|---|---|
| CH | WO88/03781 | 2/1988 |
| CH | WO93/2077 | 10/1993 |

(Continued)

OTHER PUBLICATIONS

Laney, et al, "Dental Implants: Tissue-Integrated Prosthesis Utilizing the Osseointegration Concept," Mayo Clinic, Feb. 1986, vol. 61, Issue 2, pp. 91-97.

(Continued)

*Primary Examiner* — Christopher Beccia
(74) *Attorney, Agent, or Firm* — Trop, Pruner & Hu, P.C.

(57) ABSTRACT

An embodiment includes an expandable intervertebral body fusion device with two expansion wedges within a generally hollow main body. After implantation into the intervertebral disc space, the expansion wedges are simultaneously moved from the center of the device toward the ends, which flexes the arms of the cage and increases the size of the implant. This expansion stabilizes the device in the disc space and increases the disc height, thereby reducing foraminal compression of spinal nerves and creating a stable motion segment for eventual fusion. Other embodiments are described herein.

25 Claims, 4 Drawing Sheets

(56) References Cited

U.S. PATENT DOCUMENTS

| | | |
|---|---|---|
| 2,721,387 A | 10/1955 | Ashuckian |
| 3,435,526 A | 4/1969 | Brancato |
| 3,499,222 A | 3/1970 | Linkow |
| 3,579,831 A | 5/1971 | Stevens |
| 3,623,396 A | 11/1971 | Mortensen |
| 3,708,883 A | 1/1973 | Flander |
| 3,848,601 A | 11/1974 | Ma |
| 3,905,109 A | 9/1975 | Cohen |
| 4,011,602 A | 3/1977 | Rybicki |
| 4,013,071 A | 3/1977 | Rosenberg |
| 4,349,921 A | 9/1982 | Kuntz |
| 4,431,416 A | 2/1984 | Niznick |
| 4,484,570 A | 11/1984 | Sutter |
| 4,501,269 A | 2/1985 | Bagby |
| 4,523,587 A | 6/1985 | Frey |
| 4,588,381 A | 5/1986 | Caracciolo |
| 4,653,132 A | 3/1987 | Yamada |
| 4,714,469 A | 12/1987 | Kenna |
| 4,722,688 A | 2/1988 | Lonca |
| 4,743,256 A | 5/1988 | Brantigan |
| 4,834,757 A | 5/1989 | Brantigan |
| 4,877,020 A | 10/1989 | Vich |
| 4,878,915 A | 11/1989 | Brantigan |
| 4,932,868 A | 6/1990 | Linkow |
| 4,936,848 A | 6/1990 | Bagby |
| 4,961,740 A | 10/1990 | Ray |
| 5,004,421 A | 4/1991 | Lazarof |
| 5,013,242 A | 5/1991 | Prezmecky |
| 5,015,247 A | 5/1991 | Michelson |
| 5,017,067 A | 5/1991 | Ohlin |
| 5,023,990 A | 6/1991 | Lee |
| 5,026,373 A | 6/1991 | Ray |
| 5,055,104 A | 10/1991 | Ray |
| 5,059,193 A | 10/1991 | Kuslich |
| 5,061,181 A | 10/1991 | Niznick |
| 5,087,199 A | 2/1992 | Lazarof |
| 5,108,395 A | 4/1992 | Laurain |
| 5,192,327 A | 3/1993 | Brantigan |
| 5,209,753 A | 5/1993 | Biedermann |
| 5,217,497 A | 6/1993 | Mehdian |
| 5,259,398 A | 11/1993 | Vrespa |
| 5,269,685 A | 12/1993 | Jorneus |
| 5,282,861 A | 2/1994 | Kaplan |
| 5,360,450 A | 11/1994 | Giannini |
| 5,390,683 A | 2/1995 | Pisharodi |
| 5,397,364 A | 3/1995 | Kozak |
| 5,443,514 A | 8/1995 | Steffee |
| 5,458,638 A | 10/1995 | Kuslich |
| 5,470,230 A | 11/1995 | Daftary |
| 5,474,555 A | 12/1995 | Puno |
| 5,484,437 A | 1/1996 | Michelson |
| 5,489,210 A | 2/1996 | Hanosh |
| 5,505,732 A | 4/1996 | Michelson |
| 5,522,899 A | 6/1996 | Michelson |
| 5,554,191 A | 9/1996 | Lahille |
| 5,591,235 A | 1/1997 | Kuslich |
| 5,593,409 A | 1/1997 | Michelson |
| 5,609,635 A | 3/1997 | Michelson |
| 5,609,636 A | 3/1997 | Kohrs |
| 5,611,688 A | 3/1997 | Hanosh |
| 5,653,763 A | 8/1997 | Errico |
| 5,658,285 A | 8/1997 | Marnay |
| 5,665,122 A | 9/1997 | Kambin |
| 5,669,909 A | 9/1997 | Zdeblick |
| 5,681,167 A | 10/1997 | Lazarof |
| 5,683,394 A | 11/1997 | Rinner |
| 5,702,393 A | 12/1997 | Pfaifer |
| 5,702,397 A | 12/1997 | Goble |
| 5,707,395 A | 1/1998 | Li |
| 5,713,904 A | 2/1998 | Errico |
| 5,723,013 A | 3/1998 | Jeanson |
| 5,725,529 A | 3/1998 | Nicholson |
| 5,725,581 A | 3/1998 | Branemark |
| 5,741,253 A | 4/1998 | Michelson |
| 5,749,916 A | 5/1998 | Richelsoph |
| 5,762,500 A | 6/1998 | Lazarof |
| 5,766,252 A | 6/1998 | Henry |
| 5,772,253 A | 6/1998 | Hodge |
| 5,772,661 A | 6/1998 | Michelson |
| 5,776,197 A | 7/1998 | Rabbe |
| 5,776,198 A | 7/1998 | Rabbe |
| 5,782,865 A | 7/1998 | Grotz |
| 5,785,710 A | 7/1998 | Michelson |
| 5,797,909 A | 8/1998 | Michelson |
| 5,853,422 A | 12/1998 | Huebsch |
| 6,080,155 A | 6/2000 | Michelson |
| 6,080,193 A | 6/2000 | Hochshuler |
| 6,083,228 A | 7/2000 | Michelson |
| 6,096,038 A | 8/2000 | Michelson |
| 6,102,950 A | 8/2000 | Vaccaro |
| 6,117,174 A | 9/2000 | Nolan |
| 6,120,503 A | 9/2000 | Michelson |
| 6,123,705 A | 9/2000 | Michelson |
| 6,126,689 A | 10/2000 | Brett |
| 6,139,551 A | 10/2000 | Michelson |
| 6,149,650 A | 11/2000 | Michelson |
| 6,179,873 B1 | 1/2001 | Zientek |
| 6,190,388 B1 | 2/2001 | Michelson |
| 6,190,414 B1 | 2/2001 | Young |
| 6,206,923 B1 | 3/2001 | Boyd |
| 6,210,412 B1 | 4/2001 | Michelson |
| 6,214,050 B1 | 4/2001 | Huene |
| 6,224,595 B1 | 5/2001 | Michelson |
| 6,264,656 B1 | 7/2001 | Michelson |
| 6,270,498 B1 | 8/2001 | Michelson |
| 6,302,914 B1 | 10/2001 | Michelson |
| 6,350,283 B1 | 2/2002 | Michelson |
| 6,371,989 B1 | 4/2002 | Chuavin |
| 6,395,031 B1 | 5/2002 | Foley |
| 6,436,140 B1 | 8/2002 | Liu |
| 6,436,142 B1 | 8/2002 | Paes |
| 6,447,544 B1 | 9/2002 | Michelson |
| 6,471,724 B2 | 10/2002 | Zdeblick |
| 6,491,724 B1 | 12/2002 | Ferree |
| 6,579,290 B1 | 6/2003 | Hardcastle |
| 6,719,796 B2 | 4/2004 | Cohen |
| 6,962,606 B2 | 11/2005 | Michelson |
| 6,972,035 B2 | 12/2005 | Michelson |
| 7,569,074 B2 | 8/2009 | Eisermann |
| 7,591,853 B2 | 9/2009 | Felt |
| D626,233 S | 10/2010 | Cipoletti |
| 7,828,848 B2 | 11/2010 | Chuavin |
| 8,029,522 B2 | 10/2011 | Ortiz |
| 8,603,170 B2 | 12/2013 | Cipoletti |
| 8,894,712 B2 | 11/2014 | Varela |
| 8,992,621 B2 | 3/2015 | Chuavin |
| 2002/0040243 A1 | 4/2002 | Attali |
| 2003/0130731 A1 | 7/2003 | Gerbec |
| 2004/0044409 A1 | 3/2004 | Alfaro |
| 2006/0241774 A1* | 10/2006 | Attali et al. ............... 623/17.16 |
| 2006/0253201 A1* | 11/2006 | McLuen .................... 623/17.15 |
| 2009/0222100 A1* | 9/2009 | Cipoletti et al. ........... 623/17.16 |
| 2009/0276048 A1 | 11/2009 | Chirico |
| 2012/0323327 A1 | 12/2012 | McAfee |
| 2012/0330360 A1 | 12/2012 | Nishida |
| 2014/0194992 A1 | 7/2014 | Medina |

FOREIGN PATENT DOCUMENTS

| | | |
|---|---|---|
| CH | WO96/16607 | 6/1995 |
| DE | 2460431 | 6/1976 |
| DE | 7701056 | 1/1977 |
| DE | 2542263 | 3/1977 |
| DE | 3615091 | 11/1987 |
| DE | 4323956 | 7/1993 |
| DE | 9407806 | 11/1994 |
| DE | 4416604 | 6/1995 |
| DE | 4416605 C1 | 6/1995 |
| EP | 0493789 | 7/1992 |
| EP | 0595782 | 5/1994 |
| EP | 0637440 | 2/1995 |
| EP | 0664994 | 8/1995 |
| EP | 0734703 | 10/1996 |
| FR | 9400860 | 1/1994 |

(56) References Cited

FOREIGN PATENT DOCUMENTS

| | | |
|---|---|---|
| FR | 2719763 | 8/1995 |
| GB | 8620937 | 2/1986 |
| GB | 2181809 | 4/1987 |
| GB | 2294399 | 1/1996 |
| JP | 60-43984 | 10/1985 |
| JP | 63-145650 | 6/1988 |
| JP | 63-300758 | 12/1988 |
| JP | 2-149271 | 6/1990 |
| JP | 3-503133 | 7/1991 |
| JP | 3-52742 | 8/1991 |
| JP | 3-63898 | 10/1991 |
| JP | 3-505416 | 11/1991 |
| JP | 3-275055 | 12/1991 |
| JP | 4-20342 | 1/1992 |
| JP | 4-42940 | 7/1992 |
| JP | 4-88929 | 8/1992 |
| JP | 5-52218 | 4/1993 |
| JP | 5-51304 | 8/1993 |
| JP | 5-269160 | 10/1993 |
| JP | 6-189991 | 7/1994 |
| JP | 6-237944 | 8/1994 |
| JP | 6-319759 | 11/1994 |
| JP | 7-7612 | 2/1995 |
| JP | 7-39557 | 2/1995 |
| JP | 7-148189 | 6/1995 |
| JP | 7-148190 | 6/1995 |
| JP | 7-275267 | 10/1995 |
| JP | 8-56971 | 3/1996 |
| JP | 8-503876 | 4/1996 |
| JP | 8-215225 | 8/1996 |
| JP | 2551670 | 8/1996 |
| JP | 8-266563 | 10/1996 |
| JP | 8-266564 | 10/1996 |
| JP | 8-266565 | 10/1996 |
| JP | 8-294495 | 11/1996 |
| JP | 8-511701 | 12/1996 |
| JP | 2632850 | 4/1997 |
| JP | 9-506790 | 7/1997 |
| JP | 2669379 | 7/1997 |
| JP | 10-33656 | 2/1998 |
| JP | 10-501710 | 2/1998 |
| JP | 10-99356 | 4/1998 |
| JP | 2769926 | 4/1998 |
| JP | 10-165412 | 6/1998 |
| JP | 10-179622 | 7/1998 |
| RU | 2008851 | 3/1994 |
| WO | WO96/08205 | 2/1996 |
| WO | 97/08205 | 3/1997 |
| WO | WO2005/112834 | 12/2005 |
| WO | WO2012/115631 | 8/2012 |

OTHER PUBLICATIONS

Adell, et al, "A 15-year study of osseointegrated implants in the treatment of the edentulous jaw," International Journal of Oral Surgery, vol. 10, Issue 6, 1981, pp. 387-416.

\* cited by examiner

BILATERALLY EXPANDING INTERVERTEBRAL BODY FUSION DEVICE

CROSS-REFERENCE TO RELATED APPLICATION

This application claims priority to U.S. Provisional Patent Application No. 62/007,500 filed on Jun. 4, 2014 and entitled "Bilaterally expanding intervertebral body fusion device", the content of which is hereby incorporated by reference.

TECHNICAL FIELD

Embodiments of the invention are in the field of implantable bone implants or prostheses and the surgical techniques for using them.

BACKGROUND

U.S. Pat. No. 8,435,299 describes an expandable osteosynthesis cage. An embodiment described therein concerns an implant designed to be slid or inserted from a posterior direction between the facing faces of two consecutive vertebrae in order to maintain a given distance between them and to restore the stability of the spinal column (e.g., after a failure of the corresponding joint) by fixing the two vertebrae together.

The patent addresses several techniques for restoring a "normal" lumbar lordosis such as, for example, implanting either a graft (which in time fuses the vertebrae together) or a prosthesis (which fixes them together immediately) while still also making it possible in time to achieve fusion between the vertebra. One such prosthesis is a "cage", which is hollow and rigid with inside/outside intercommunication slots for receiving a bone graft which, via the slots, subsequently fuses with the adjacent vertebrae on either side.

The patent addresses various types of cages including those having two substantially parallel branches connected to a rigid body through which it is possible to turn a worm screw system. The worm screw system then moves a wedge in screw engagement on the screw from an initial position close to the distal ends of the branches towards the body linking the branches together, thereby splaying the two branches apart angularly. It is then possible to insert such a cage of initially flat shape between the vertebrae, and then by turning the drive axis of the wedge, the desired angle between the branches is adjusted or set from a posterior access. Such devices are more complex mechanically and leave a smaller inside volume for the fusion graft. Also, because of their flat shape even though they are better at ensuring a given bearing angle between the vertebrae, they require a passage of the same rectangular section to be prepared to receive them, and that complicates implementation.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. Additional structures known in the art may not have been included to maintain the clarity of the drawings. In the following description, numerous specific details are set forth but embodiments of the invention may be practiced without these specific details. Well-known structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Figure 1A:
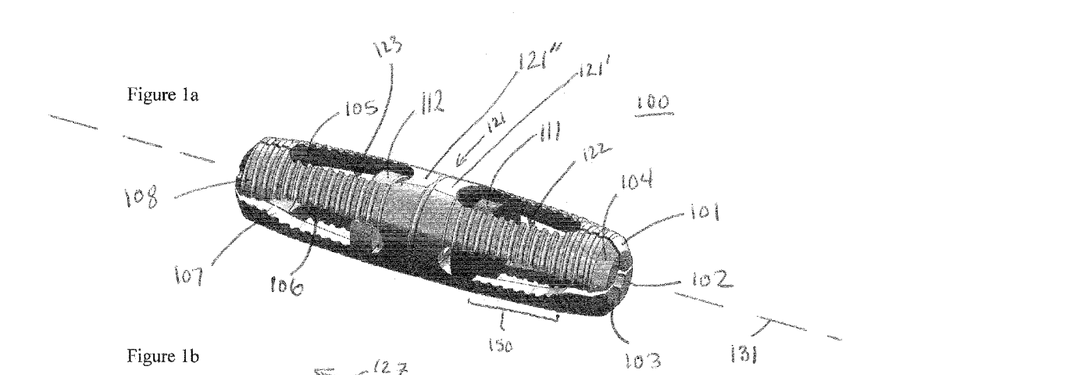
FIG. 1a includes a perspective view of an embodiment shown in its "unexpanded" state.
Figure 1B:
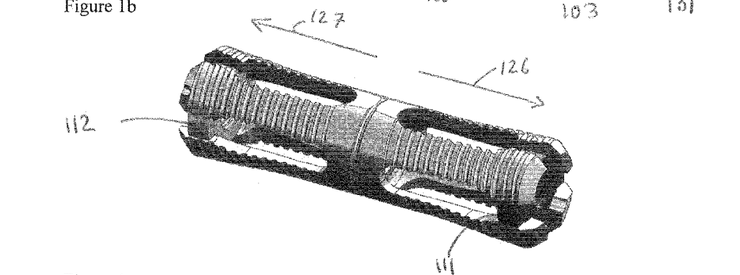
FIG. 1b includes a perspective view of the embodiment of FIG. 1a shown in its "expanded" state.
Figure 1C:
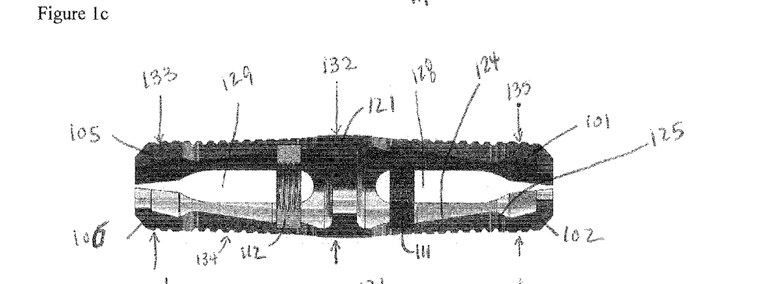
FIG. 1c includes a cross section of the embodiment of FIG. 1a shown with wedges in "unexpanded" position.
Figure 1D:
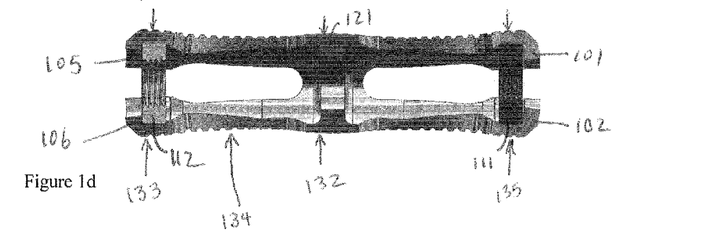
FIG. 1d includes a cross section of the embodiment of FIG. 1a shown with wedges in "expanded" position.

FIG. 1a includes a perspective view of an embodiment shown in its "unexpanded" state. FIG. 1b includes a perspective view of the embodiment of FIG. 1a shown in its "expanded" state. FIG. 1c includes a cross section of the embodiment of FIG. 1a shown with wedges in "unexpanded" position. FIG. 1d includes a cross section of the embodiment of FIG. 1a shown with wedges in "expanded" position.

An embodiment consists of an expandable intervertebral body fusion device 100 with two expansion wedges 111, 112 within a generally hollow main body. After implantation into the intervertebral disc space, the expansion wedges are simultaneously moved from the center of the device toward the lateral ends, which flexes the arms 101, 102, 103, 104, 105, 106, 107, 108 of the cage 100 and increases the size of the implant. This expansion stabilizes the device in the disc space and increases the disc height, thereby reducing foraminal compression of spinal nerves and creating a stable motion segment for eventual fusion.

Many examples of conventional technology limit expansion features to only one end of the intervertebral fusion device. This limits the orientation of the device to be in a primarily anterior-posterior direction to replicate the physiological curvature of the spine. In contrast, an embodiment permits simultaneous bilateral expansion of the intervertebral fusion device. The cage 100 can be oriented in a lateral or oblique orientation in the disc space, and will not induce any or much scoliotic angle after expansion. Such a cage may be referred to as a direct lateral interbody fusion (DLIF) cage, indicating the cage is specifically configured for a lateral approach.

Expandable intervertebral body fusion device 100 consists of a main body with multiple flexible arms (also called branches) 101, 102, 103, 104, 105, 106, 107, 108 originating from the center of the device, and extending generally parallel to the long axis 131 of the body. Within the body, and between the arms, are two slidable expansion wedges (also called spacers) 111, 112 which, when translated from the center of the body toward the ends, force the arms to flex radially outward. This increases the effective size of the device.

Figure 2A:
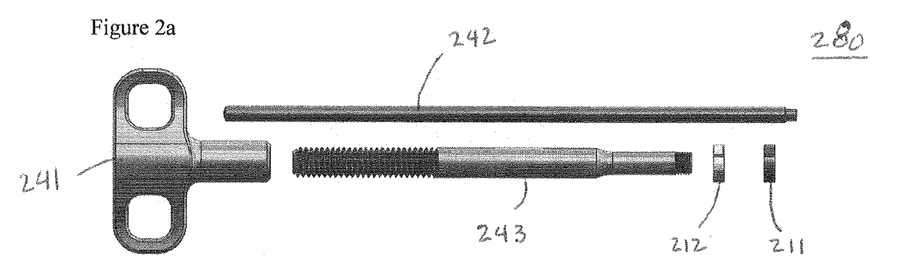
FIG. 2a includes a disassembled embodiment of an implant system.
Figure 2B:
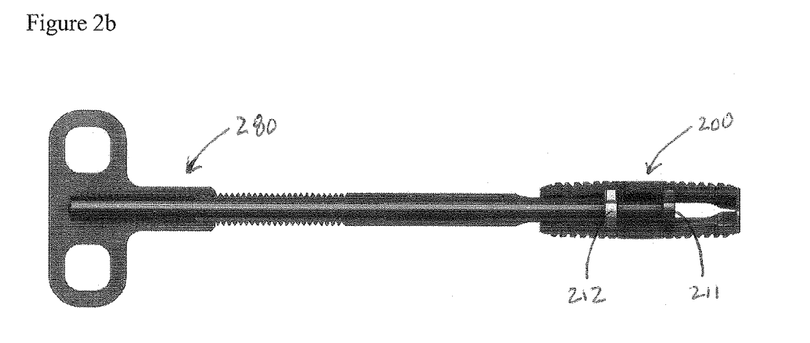
FIG. 2b includes an assembled embodiment of an implant system in its unexpanded form.
Figure 2C:
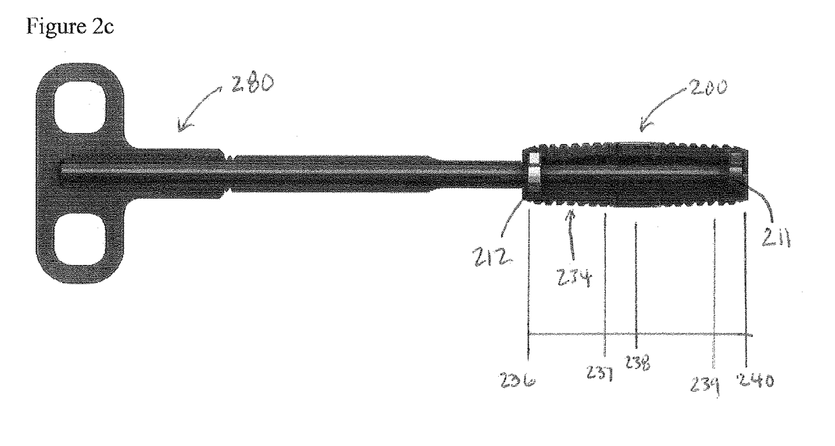
FIG. 2c includes an assembled embodiment of an implant system in its expanded form.

FIG. 2a includes a disassembled embodiment of an implant system. FIG. 2b includes an assembled embodiment of an implant system in its unexpanded form. FIG. 2c includes an assembled embodiment of an implant system in its expanded form.

In FIG. 2b, translation of the wedges 211, 212 is accomplished by instrument system 280, a portion of which (rods 242, 243) are inserted through one end of the body, and attach to each wedge. One instrument 242 pushes on the distal wedge 211, while another instrument 243 simultaneously pulls on the proximal wedge 212. Instrument 243 may be referred to as a "proximal expander" that is attached to the proximal wedge 212. Instrument 242 may be referred to as a "distal expander" that is attached to the distal wedge 211 after being inserted through proximal expander 243. Portion 241 may be referred to as "expander knob" and may be threaded onto proximal expander 243. As knob 241 is rotated and threads onto proximal expander 243, it simultaneously pushes on distal wedge 211 and pulls on proximal wedge 212 until both wedges fully advance towards ends of interbody device 100. Threads 234 helps "screw" the implant into position by traversing the vertebrae.

An embodiment facilitates fusion of an intervertebral disc space. Specifically, the length permitted by the design of cage 100, along the symmetric expansion capability (described below in conjunction with FIGS. 4a-e, allows for a direct lateral surgical approach to the intervertebral disc. However, an embodiment is not so limited and may be used for fracture stabilization, fusion of the sacro-iliac joint, facet joint fixation, and the like.

The embodiment of FIG. 1 describes a generally cylindrical, threaded device. Cage 100 may be implanted into the intervertebral disc space by rotation, whereby the threads 150 advance the cage 100 until final placement is achieved.

Figure 3A:
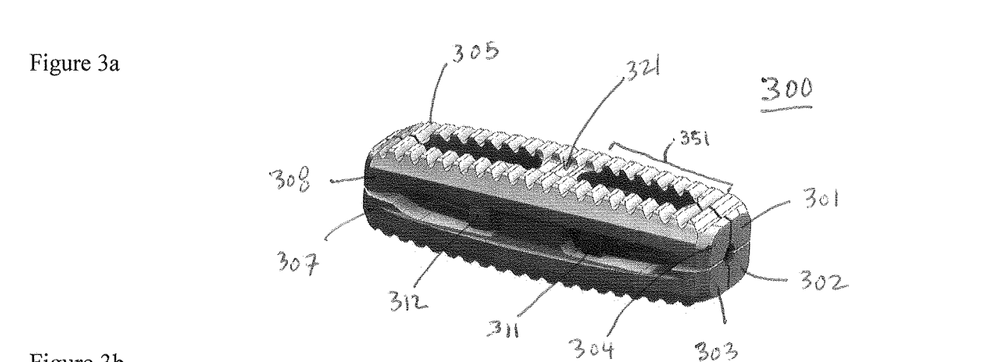
FIG. 3a includes a perspective view of an embodiment shown in its "unexpanded" state.
Figure 3B:
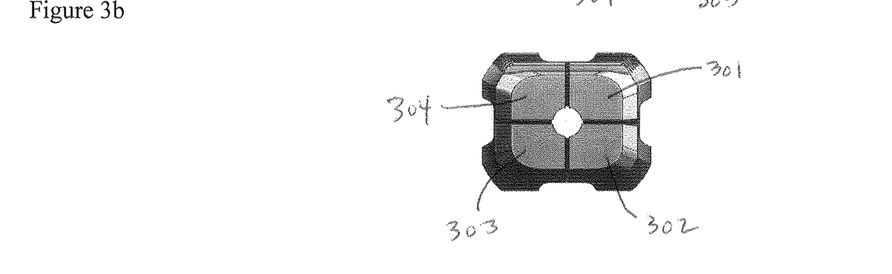
FIG. 3b includes a front view of the embodiment of FIG. 3a in its unexpanded state.

FIG. 3a includes a perspective view of an embodiment shown in its "unexpanded" state. FIG. 3b includes a front view of the embodiment of FIG. 3a in its unexpanded state.

An embodiment includes a device 300 which has the same overall dimensions as cage 100, but is generally rectangular in cross-section. Rather than threads 150, the device has "teeth" 351 on the inferior and superior surfaces, intended to grip adjacent vertebral end plates. The embodiment is advanced into the intervertebral disc space by impaction on the proximal face of the implant rather than by rotation. Cage 300 includes first branches 301, 302, 303, 304 and second branches 305, 307, 308 and another branch not easily seen in FIG. 3a.

Returning to FIG. 1a, cage 100 has expansion wedges 111, 112 that are circular in cross section, and a body which has an internal bore with circular or conical cross section. This provides for equal expansion of arms 101, 102, 103, 104, 105, 106, 107, 108 in both anterior and posterior directions as well as superior and inferior directions. An alternative embodiment has elliptical or rectangular cross sections (or generally asymmetric) for either the wedges and/or interior ramps (e.g., some ramps are thicker than other ramps with thicker ramps to cause greater expansion of their corresponding branches) and cross-sections upon which the wedges traverse. As described immediately below, this allows for differential expansion of the arms (e.g., arms expand more in the anterior/posterior directions than in the superior/inferior directions, or vice-versa).

Figure 4A:
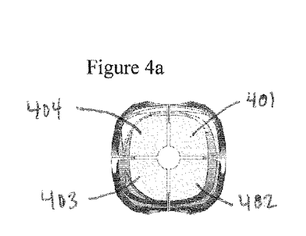
FIG. 4a includes a front view of an embodiment in its unexpanded state.
Figure 4B:
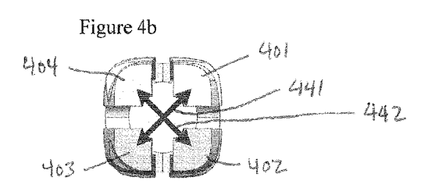
FIG. 4b includes a front view of the embodiment of FIG. 4a having undergone symmetric bilateral expansion.
Figure 4C:
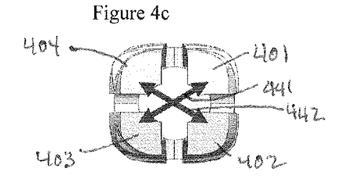
FIG. 4c includes a front view of the embodiment of FIG. 4a having undergone lateral expansion greater than vertical expansion.
Figure 4D:
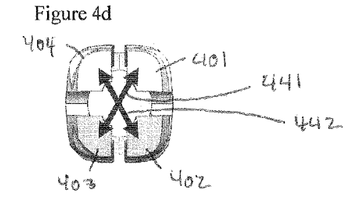
FIG. 4d includes a front view of the embodiment of FIG. 4a having undergone vertical expansion greater than horizontal expansion.

FIG. 4a includes a front view of an embodiment in its unexpanded state. FIG. 4b includes a front view of the embodiment of FIG. 4a with arms 401, 402, 403, 404 having undergone symmetric expansion. FIG. 4c includes a front view of the embodiment of FIG. 4a having undergone lateral expansion that is greater than vertical expansion. In other words, expansion along lines 441, 442 are greater horizontally (anterior/posterior) than vertically (superior/inferior). FIG. 4d includes a front view of the embodiment of FIG. 4a having undergone vertical expansion that is greater than horizontal expansion. In other words, expansion along lines 441, 442 are lesser horizontally (anterior/posterior) than vertically (superior/inferior).

Figure 4E:
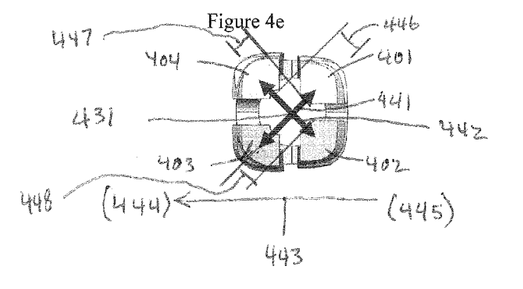
FIG. 4e includes a front view of the embodiment of FIG. 4a having undergone unequal expansion amongst the branches.

FIG. 4e includes a front view of the embodiment of FIG. 4a having undergone unequal expansion. In other words, expansion along lines 441, 442 are greater horizontally (anterior/posterior) and vertically (superior/inferior) for arms 403, 404 than for arms 401, 402. For example, greater expansion with a device such as the one shown in FIG. 4e may provide for greater expansion to the anterior side in the lumbar region. In FIG. 4(e) direction 443 may provide that location 444 is anterior in some embodiments or inferior in other embodiments whereas location 445 may be posterior in some embodiment or superior in other embodiments.

Still referring to FIG. 4e for example, one of the first branches (e.g., branch 404) deflects radially a first distance from the long axis (i.e., where first distance is taken orthogonal to axis 431) when the first spacer is secured by the one or more first shoulders (i.e., upon full deployment of spacer to its lateral-most position); wherein another of the first branches (e.g., branch 401) deflects radially a second distance from the long axis (i.e., where second distance is taken orthogonal to axis 431) when the first spacer is secured by the one or more first shoulders; wherein the first distance is unequal to the second distance. For example, branch 404 may deflect away from axis 431 to a greater extent than branch 401 because the spacer causing the branches to deflect may be non-circular in cross-section and may be more intrusive on branch 404 than branch 401. Thus, distance 446 may be greater than distance 447. In an embodiment, an additional one of the first branches is located between the one of the first branches and the another of the first branches. For example, in an embodiment branch 404 deflects from axis 431 to a greater degree than branch 402 (i.e., distance 448 is less than distance 446). In this case, branches 402, 404 are separated from each other by either or both of branches 401, 403.

Along those lines, embodiments are suitable for lumbar, thoracic, and cervical applications and surgeons may select the type of expansion desired (and the corresponding cage to use) based on the implant site (e.g., lumbar vs. thoracic).

Thus, embodiments described herein provide for a longer device than found with traditional devices that only include a single spacer or wedge advancing along an anterior/posterior route. Such an embodiment allows for expansion on both ends of device, shares physiologic loads across more points, reducing stress at each arm, and expands clinical utility of the device by allowing additional surgical approaches (e.g., lateral with a DLIF cage).

As used herein "simultaneous" just requires overlap at at least one moment time (e.g., a millisecond) of the deployment and does not necessarily require both wedges to start and/or stop deployment at an identical moment or moments in time.

An embodiment does not require simultaneous expansion but may allow for a first wedge to move into an expanded state followed by a second wedge moving into an expanded state.

An embodiment may provide simultaneous expansion that is asynchronous. For example, with FIG. 2c wedges 211 and 212 may be moving at the same time (towards locations 240, 236) but wedge 212 may be at location 237 while wedge 211 is at location 239 (wherein the distance between locations midline 238 and 237 is smaller than the distance between midline 238 and 239).

The embodiment of FIG. 1 illustrates 8 arms, 4 of which are deployed by the proximal wedge and 4 of which are deployed by the distal wedge. However, another embodiment may provide for a total of 4 arms, 2 of which are deployed by the proximal wedge and 2 of which are deployed by the distal wedge. For example, the "2 of which are deployed by the proximal wedge" may include a superior arm and an inferior arm. The superior arm and/or inferior arm may each have an aperture within said arm. That aperture may pass completely through the arm while having a perimeter completely enclosed by the arm. For example, the arm may have a torus or donut portion. The arm may include a rectangular toroid shape or toroid with rectangular cross-section (e.g., rectangle with hole passing through it). The same may be true for the arms deployed by distal wedge. In such an embodiment the tips of the arm may not splay away from each other because those tips may be connected to one another. Another embodiment does not necessarily include symmetry in the number of arms. For example, the distal portion of the embodiment may have a number of arms (e.g., 3) and the proximal portion may include more (e.g., 4 or 5) or less (2) arms.

Any of the arms discussed above may have bilateral expansion (horizontal and vertical, as seen in FIGS. 4a and 4e) or may move only vertically or horizontally (or maybe have just one arm or a few arms of several arms move/spread out during device deployment).

The following examples pertain to further embodiments.

Example 1 includes an intervertebral spacing implant system comprising a first seat having a first lateral end. Such a seat may include, for example, portion 121' of FIG. 1a with a second seat portion indicated by portion 121". Cage 100 includes first branches (101, 102, 103, 104) coupled to the first lateral end of the first seat and extending in a first lateral direction away from the first seat. The first seat and the first branches form a first cage defining a first internal volume. Such a volume is indicated by volume 122 with a corresponding volume at 123. Each first branch has a first inward side and a first outward side. FIG. 1c indicates branch or arm 102 having a ramp 124 as well as smooth, non-threaded shoulder 125. A first spacer (e.g., spacer 111) is configured to fit within the first cage and move in the first lateral direction (e.g., direction 126) upon the urging of a spacer-advancing instrument (e.g., system 280 of FIG. 2), the first spacer and first cage configured such that one or more first branches will move from an unextended position to an extended position when the first spacer is urged in the first lateral direction; one or more first shoulders (e.g., shoulder 125) formed on the first inward side of one or more first branches, the one or more first shoulders configured to reversibly secure the first spacer near a first lateral end of the first branches. By being reversible, this allows for a spacer to be withdrawn or moved to center of cage 100 (i.e., towards seat 121). The spacer can be reversible based on contour edges of both the spacer (not shown) and/or shoulder (e.g., shoulder 125). The first internal volume between the first lateral end of the first seat and the first spacer is unoccupied by any link member when the first spacer is secured by the one or more first shoulders. The second cage comprising arms 105, 105, 107, 108 functions similarly to the first cage including arms 101, 102, 103, 104. The embodiment may include a second seat (e.g., portion 121") having a second lateral end; second branches coupled to the second lateral end of the second seat and extending in a second lateral direction (e.g., direction 127) away from the second seat, the second seat and the second branches forming a second cage defining a second internal volume, each second branch having a second inward side and a second outward side; a second spacer configured to fit within the second cage and move in the second lateral direction upon the urging of the spacer-advancing instrument, the second spacer and the second cage configured such that one or more second branches will move from an unextended position to an extended position when the second spacer is urged in the second lateral direction; one or more second shoulders formed on the inward side of one or more second branches, the one or more second shoulders configured to reversibly secure the second spacer near a second lateral end of the second plurality of branches; wherein the second internal volume between the second proximal end of the second seat and the second spacer is unoccupied by any link member when the second spacer is secured by the one or more second shoulders; wherein the first seat, second seat, first branches, and second branches are all monolithic with each other. Thus, portions 121', 121", and arms 101, 102, 103, 104, 105, 106, 107, 108 are all formed from a single element without welds, adhesives, and the like (i.e. monolithic). For example, the portions are machined from a single block of material, such as titanium or steel.

In example 2 the subject matter of the Example 1 can optionally include wherein an outside general shape of each of the first and second cages is at least one of cylindrical and quasi-cylindrical when the first and second branches are in an unextended position; wherein an outside general shape of the first and second cages is frustoconical, flaring away respectively from the first and second seats, when one or more first and second branches are in an extended position. An embodiment includes an outside general shape of each of the first and second cages as being ovoid or quasi-ovoid.

In some embodiments, the lateral ends may have heights 133, 135 that are less than height 132 of seat 121 before expansion (FIG. 1c). However, the lateral ends may have heights 133, 135 that are greater than height 132 of seat 121 after expansion (FIG. 1d). Further, outside walls such as the area populated by threads 134 may be bowed or curved before expansion with the curvature removed after expansion while in other embodiments the outside walls such as the area populated by threads 134 may be bowed or curved after expansion with the curvature removed before expansion. Such embodiments may have varying load ratings and may be more appropriate for different locations (e.g., cervical vs. lumbar).

In example 3 the subject matter of the Examples 1-2 can optionally include wherein the spacer-advancing instrument is configured to simultaneously advance the first and second spacers in the first and second lateral directions in response to rotating a portion of the spacer-advancing instrument.

Other embodiments may deploy the first and second spacers in differing ways. For example, a ratchet system with a "trigger" system may be used to manipulate cage deployment modules, such as units 242, 243 of FIG. 2*a* (i.e., without necessarily requiring rotation of any instrument portion).

In example 4 the subject matter of the Examples 1-3 can optionally include wherein the spacer-advancing instrument is configured to asynchronously and simultaneously laterally advance the first and second spacers in response to rotating a portion of the spacer-advancing instrument.

In example 5 the subject matter of the Examples 1-4 can optionally include wherein the first and second cages comprise a direct lateral interbody fusion (DLIF) cage.

In example 6 the subject matter of the Examples 1-5 can optionally include wherein the first inward side of each first branch and the second inward side of each second branch is smooth and is not threaded.

In example 7 the subject matter of the Examples 1-6 can optionally include wherein a long axis (e.g., axis 131) extends centrally within the first and second cages along the first and second lateral directions (e.g., directions 126, 127); wherein one of the first branches deflects radially a first distance from the long axis when the first spacer is secured by the one or more first shoulders; wherein another of the first branches deflects radially a second distance from the long axis when the first spacer is secured by the one or more first shoulders; wherein the first distance is unequal to the second distance.

In example 8 the subject matter of the Examples 1-7 can optionally include wherein an additional one of the first branches is located between the one of the first branches and the another of the first branches.

In example 9 the subject matter of the Examples 1-8 can optionally include wherein the first and second seats each include a cross-sectional profile, in a plane orthogonal to the long axis, which is substantially cylindrical. For example, FIG. 1*a* has a "generally" or "substantially" cylindrical cross-section at seat 121, or seat portions 121', 121" (regardless of small flat portions shown in FIG. 1*a*). In fact, those cross-sections are generally or substantially circular, whereas the seat 321 of cage 300 in FIG. 3*a* has a generally cylindrical cross-section seat 321 but does not have a generally or substantially circular cross-section.

In example 10 the subject matter of the Examples 1-9 can optionally include wherein the first branches that move from an unextended position to an extended position when the first spacer is urged in the first lateral direction further comprise the first one or more shoulders; wherein the first spacer comprises a first connector (e.g., internal threads for spacer 111) to removably couple the first spacer to the spacer-advancing instrument; wherein the second branches that move from an unextended position to an extended position when the second spacer is urged in the second lateral direction further comprise the second one or more shoulders; wherein the second spacer comprises a second connector to removably couple the second spacer to the spacer-advancing instrument.

In example 11 the subject matter of the Examples 1-10 can optionally include wherein the first branches are configured to enable bilateral expansion of the implant and the second branches are configured to enable bilateral expansion of the implant.

In example 12 the subject matter of the Examples 1-11 can optionally include a first orifice extending from the first internal volume (e.g., space 122) of the first cage and through the first seat (e.g., portion 121') to the second seat (e.g., portion 121"), the orifice configured to allow the spacer-advancing instrument to pass through; a second orifice extending from the second internal volume (e.g., space 123) of the second cage and through the second seat to the first seat, the second orifice configured to allow the spacer-advancing instrument to pass through.

As used herein, a first seat and a second seat may be portions of a larger surface. For example, portions 121' and 121" are both portions of surface 121. Thus, the first and second cages of Example 1 may be referred to as first and second cage portions.

In example 13 the subject matter of the Examples 1-12 can optionally include a plug, wherein at least one of the first and second spacers includes an orifice configured to sealingly mate with the plug. For example, spacer 112 of FIG. 1*d* has internal threads to mate with insertion device 200 of FIG. 2*a*. After spacer 112 is fully laterally deployed bone particulate or other graft/bone generating material may be placed in spaces 122, 123. Afterwards, a plug may be added to aperture within spacer 112 to seal the space 123 and pack the bone generating material within cage 100. An embodiment may include another plug to fit within the orifice of spacer 111 (or a plug for spacer 111 but not spacer 112).

In example 14 the subject matter of the Examples 1-13 can optionally include wherein at least a portion of the first internal volume is in the form of a truncated cone when the first branches are in an unextended position; wherein at least a portion of the second internal volume is in the form of a truncated cone when the second branches are in an unextended position.

In example 15 the subject matter of the Examples 1-14 can optionally include wherein the implant comprises a first plurality of spacers for the first cage and a second plurality of cages for the second cage. The additional spacers may have a terminal or fully deployed stage midway along the proximal and distal cages to provide greater support.

In example 16 the subject matter of the Examples 1-14 can optionally include wherein the first seat comprises one or more first flat surfaces (e.g., portion 121') between the second seat and the first lateral end; wherein the second seat comprises one or more second flat surfaces (e.g., portion 121") between the first seat and the second lateral end.

In example 17 the subject matter of the Examples 1-16 can optionally include wherein a first medial edge of a perimeter of the first spacer is tapered; wherein a second medial edge of a perimeter of the second spacer is tapered. Thus, for inner edges of spacers (edges closest to seat) may be tapered to help promote reversibility so a fully deployed spacer can be withdrawn and the cage can be collapsed (fully or partially).

In example 18 the subject matter of the Examples 1-17 can optionally include wherein the first seat and first branches form a unitary structure and the second seat and second branches form a second unitary structure.

In example 19 the subject matter of the Examples 1-18 can optionally include wherein two of the first branches partially define a first slot (e.g., slot 128) configured to allow fusion between graft material and a vertebra; wherein two of the second branches partially define a second slot (e.g., slot 129) configured to allow fusion between the graft material and the vertebra.

In example 20 the subject matter of the Examples 1-19 can optionally include wherein the first seat, the first spacer, and the two first branches define the first slot when one or more first branches are in an extended position; wherein the second seat, the second spacer, and the two second branches define the second slot when one or more second branches are in an extended position.

In example 21 the subject matter of the Examples 1-20 can optionally include wherein an additional two of the first branches partially define an additional slot configured to allow fusion between the graft material and an additional vertebra.

In example 22 the subject matter of the Examples 1-21 can optionally include wherein the first seat, the first spacer, and the first additional two branches define the additional slot when one or more first branches are in an extended position.

In example 23 the subject matter of the Examples 1-22 can optionally include wherein the first branches comprise three or more branches and the second branches comprise three or more branches; wherein the first lateral ends of two or more first branches may connect to one another and second lateral ends of two or more of the second branches connect to one another; wherein at least a portion of the outward side of one or more first branches comprises ridges; wherein the extended position is an active position and the unextended position is a rest position.

In example 24 the subject matter of the Examples 1-23 can optionally include the spacer-advancing instrument, wherein the spacer-advancing instrument includes a plurality of threaded rods.

In example 25 the subject matter of the Examples 1-24 can optionally include wherein the spacer-advancing instrument is configured to simultaneously advance the first and second spacers in the first and second lateral directions in response to advancing a pushing module in at least one of the first and second lateral directions. For example, a trigger based ratchet system may include a module, such as a rod configured to mate with a spacer and advance or withdraw the spacer.

In example 25 the subject matter of the Examples 1-24 can optionally include wherein a first lateral-most edge portion of the first branches has a first unexpanded height when the first spacer is not secured by the one or more first shoulders and a first expanded height when the first spacer is secured by the one or more first shoulders; wherein a second lateral-most edge portion of the second branches has a second unexpanded height when the second spacer is not secured by the one or more second shoulders and a second expanded height when the second spacer is secured by the one or more second shoulders; wherein the first seat has a first seat height; wherein the first seat height is (a) greater than the first and second unexpanded heights, and (b) less than the first and second expanded heights.

For example, height 132 is greater than height 133, 135 of FIG. 1c but less than height 133, 135 of FIG. 1d. In other embodiments (not shown), height 132 is greater than height 133, 135 of FIG. 1c but substantially (+/−5%) equal to height 133, 135 of FIG. 1d. In other embodiments (not shown), height 132 is substantially (+/−5%) equal to height 133, 135 of FIG. 1c but less than height 133, 135 of FIG. 1d.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An intervertebral spacing implant system comprising:
   a first seat having a first lateral end;
   first branches coupled to the first lateral end of the first seat and extending in a first lateral direction away from the first seat, the first seat and the first branches forming a first cage defining a first internal volume, each first branch having a first inward side and a first outward side;
   a first spacer configured to fit within the first cage and move in the first lateral direction upon the urging of a spacer-advancing instrument, the first spacer and first cage configured such that one or more first branches will move from an unextended position to an extended position when the first spacer is urged in the first lateral direction;
   one or more first shoulders formed on the first inward side of one or more first branches, the one or more first shoulders configured to reversibly secure the first spacer near a first lateral end of the first branches;
   wherein the first internal volume between the first lateral end of the first seat and the first spacer is unoccupied by any link member when the first spacer is secured by the one or more first shoulders;
   a second seat having a second lateral end;
   second branches coupled to the second lateral end of the second seat and extending in a second lateral direction away from the second seat, the second seat and the second branches forming a second cage defining a second internal volume, each second branch having a second inward side and a second outward side;
   a second spacer configured to fit within the second cage and move in the second lateral direction upon the urging of the spacer-advancing instrument, the second spacer and the second cage configured such that one or more second branches will move from an unextended position to an extended position when the second spacer is urged in the second lateral direction;
   one or more second shoulders formed on the inward side of one or more second branches, the one or more second shoulders configured to reversibly secure the second spacer near a second lateral end of the second plurality of branches;
   wherein the second internal volume between the second proximal end of the second seat and the second spacer is unoccupied by any link member when the second spacer is secured by the one or more second shoulders;
   wherein the first seat, second seat, first branches, and second branches are all monolithic with each other.

2. The intervertebral spacing implant system of claim 1,
   wherein an outside general shape of each of the first and second cages is at least one of cylindrical and quasi-cylindrical when the first and second branches are in an unextended position;
   wherein an outside general shape of the first and second cages is frustoconical, flaring away respectively from the first and second seats, when one or more first and second branches are in an extended position.

3. The intervertebral spacing implant system of claim 1, wherein the spacer-advancing instrument is configured to simultaneously advance the first and second spacers in the first and second lateral directions in response to rotating a portion of the spacer-advancing instrument.

4. The intervertebral spacing implant system of claim 3, wherein the spacer-advancing instrument is configured to asynchronously and simultaneously laterally advance the first and second spacers in response to rotating a portion of the spacer-advancing instrument.

5. The intervertebral spacing implant system of claim 3, wherein the first and second cages comprise a direct lateral interbody fusion (DLIF) cage.

6. The intervertebral spacing implant system of claim 5, wherein the first inward side of each first branch and the second inward side of each second branch is smooth and is not threaded.

7. The intervertebral spacing implant system of claim 1,
   wherein a long axis extends centrally within the first and second cages along the first and second lateral directions;

wherein one of the first branches deflects radially a first distance, orthogonal to the long axis, when the first spacer is secured by the one or more first shoulders;

wherein another of the first branches deflects radially a second distance, orthogonal to the long axis, when the first spacer is secured by the one or more first shoulders;

wherein the first distance is unequal to the second distance.

8. The intervertebral spacing implant system of claim 7, wherein an additional one of the first branches is located between the one of the first branches and the another of the first branches.

9. The intervertebral spacing implant system of claim 7, wherein the first and second seats each include a cross-sectional profile, in a plane orthogonal to the long axis, that is substantially cylindrical.

10. The intervertebral spacing implant system of claim 1, wherein the first branches that move from an unextended position to an extended position when the first spacer is urged in the first lateral direction further comprise the one or more first shoulders;

wherein the first spacer comprises a first connector to removably couple the first spacer to the spacer-advancing instrument;

wherein the second branches that move from an unextended position to an extended position when the second spacer is urged in the second lateral direction further comprise the one or more second shoulders;

wherein the second spacer comprises a second connector to removably couple the second spacer to the spacer-advancing instrument.

11. The intervertebral spacing implant system of claim 1, wherein the first branches are configured to enable bilateral expansion of the implant and the second branches are configured to enable bilateral expansion of the implant.

12. The intervertebral spacing implant system of claim 1 comprising:

a first orifice extending from the first internal volume of the first cage and through the first seat to the second seat, the first orifice configured to allow the spacer-advancing instrument to pass through;

a second orifice extending from the second internal volume of the second cage and through the second seat to the first seat, the second orifice configured to allow the spacer-advancing instrument to pass through wherein the first and second seats are non-resilient.

13. The intervertebral spacing implant system of claim 1 comprising a plug, wherein at least one of the first and second spacers includes an orifice configured to sealingly mate with the plug.

14. The intervertebral spacing implant system of claim 1, wherein at least a portion of the first internal volume is in the form of a truncated cone when the first branches are in an unextended position;

wherein at least a portion of the second internal volume is in the form of a truncated cone when the second branches are in an unextended position.

15. The intervertebral spacing implant system of claim 1, wherein a first lateral-most edge portion of the first branches has a first unexpanded height when the first spacer is not secured by the one or more first shoulders and a first expanded height when the first spacer is secured by the one or more first shoulders;

wherein a second lateral-most edge portion of the second branches has a second unexpanded height when the second spacer is not secured by the one or more second shoulders and a second expanded height when the second spacer is secured by the one or more second shoulders;

wherein the first seat has a first seat height;

wherein the first seat height is (a) greater than the first and second unexpanded heights, and (b) less than the first and second expanded heights.

16. The intervertebral spacing implant system of claim 1, wherein the first seat comprises one or more first flat surfaces between the second seat and the first lateral end;

wherein the second seat comprises one or more second flat surfaces between the first seat and the second lateral end.

17. The intervertebral spacing implant system of claim 1, wherein a first medial edge of a perimeter of the first spacer is tapered;

wherein a second medial edge of a perimeter of the second spacer is tapered.

18. The intervertebral spacing implant of claim 1, wherein the first seat and first branches form a unitary structure and the second seat and second branches form a second unitary structure.

19. The intervertebral spacing implant system of claim 1, wherein two of the first branches partially define a first slot configured to allow fusion between graft material and a vertebra;

wherein two of the second branches partially define a second slot configured to allow fusion between the graft material and the vertebra.

20. The intervertebral spacing implant system of claim 19, wherein the first seat, the first spacer, and the two first branches define the first slot when one or more first branches are in an extended position;

wherein the second seat, the second spacer, and the two second branches define the second slot when one or more second branches are in an extended position.

21. The intervertebral spacing implant system of claim 20, wherein:

an additional two of the first branches partially define an additional slot configured to allow fusion between the graft material and an additional vertebra;

the first seat, the first spacer, and additional two of the first branches define the additional slot when one or more first branches are in an extended position.

22. The intervertebral spacing implant system of claim 21, wherein the first branches comprise three or more branches and the second branches comprise three or more branches;

wherein the first lateral ends of two or more first branches connect to one another and second lateral ends of two or more of the second branches connect to one another;

wherein at least a portion of the first outward side of one or more first branches comprises ridges;

wherein the extended position is an active position and the unextended position is a rest position;

wherein the implant comprises a first plurality of spacers for the first cage and a second plurality of spacers for the second cage.

23. The intervertebral spacing implant system of claim 1 comprising the spacer-advancing instrument, wherein the spacer-advancing instrument includes a plurality of threaded rods.

24. The intervertebral spacing implant system of claim 1, wherein the spacer-advancing instrument is configured to simultaneously advance the first and second spacers in the first and second lateral directions in response to advancing a pushing module in at least one of the first and second lateral directions.

25. An intervertebral spacing implant system comprising:
a first seat having a first lateral end;
first branches coupled to the first lateral end of the first seat and extending in a first lateral direction away from the first seat, the first seat and the first branches forming a first cage defining a first internal volume, each first branch having a first inward side and a first outward side;
a first spacer configured to fit within the first cage and move laterally in the first lateral direction upon the urging of a spacer-advancing instrument, the first spacer and first cage configured such that one or more first branches will move from an unextended position to an extended position when the first spacer is urged in the first lateral direction;
one or more first shoulders formed on the first inward side of one or more first branches, the one or more first shoulders configured to reversibly secure the first spacer near a first lateral end of the first branches;
wherein the first internal volume between the first lateral end of the first seat and the first spacer is unoccupied by any link member when the first spacer is secured by the one or more first shoulders;
a second seat having a second lateral end;
second branches coupled to the second lateral end of the second seat and extending in a second lateral direction away from the second seat, the second seat and the second branches forming a second cage defining a second internal volume, each second branch having a second inward side and a second outward side;
a second spacer configured to fit within the second cage and move laterally in the second lateral direction upon the urging of the spacer-advancing instrument, the second spacer and the second cage configured such that one or more second branches will move from an unextended position to an extended position when the second spacer is urged in the second lateral direction;
one or more second shoulders formed on the inward side of one or more second branches, the one or more second shoulders configured to reversibly secure the second spacer near a second lateral end of the second plurality of branches;
wherein the second internal volume between the second proximal end of the second seat and the second spacer is unoccupied by any link member when the second spacer is secured by the one or more second shoulders;
wherein the first seat, second seat, first branches, and second branches are all monolithic with each other;
wherein the second lateral direction is opposite the first lateral direction;
wherein the first and second seats are non-resilient and directly contact each other at a point equidistant from the first lateral end of the first branches and the second lateral end of the second plurality of branches.

* * * * *